(12) United States Patent
VanderGheynst et al.

(10) Patent No.: US 7,485,451 B2
(45) Date of Patent: Feb. 3, 2009

(54) STORAGE STABLE COMPOSITIONS OF BIOLOGICAL MATERIALS

(75) Inventors: Jean S. VanderGheynst, Davis, CA (US); Herbert B. Scher, Moraga, CA (US)

(73) Assignee: Regents of the University of California, Oakland, CA (US)

( * ) Notice: Subject to any disclaimer, the term of this patent is extended or adjusted under 35 U.S.C. 154(b) by 236 days.

(21) Appl. No.: 10/993,942

(22) Filed: Nov. 18, 2004

(65) Prior Publication Data

US 2009/0010890 A1 Jan. 8, 2009

(51) Int. Cl.
*C12P 1/12* (2006.01)
(52) U.S. Cl. .............. 435/257.4; 424/93.4; 424/195.17; 435/252.1; 435/257.1
(58) Field of Classification Search ........................ None
See application file for complete search history.

(56) References Cited

U.S. PATENT DOCUMENTS

| | | | |
|---|---|---|---|
| 5,945,099 A | 8/1999 | Marshall | |
| 6,512,012 B1 | 1/2003 | Levy | |
| 7,025,966 B2 * | 4/2006 | Majmudar | 424/195.17 |
| 7,186,673 B2 * | 3/2007 | Varadaraj et al. | 507/200 |
| 7,303,753 B2 * | 12/2007 | Majmudar | 424/195.17 |
| 2002/0159980 A1 | 10/2002 | Block et al. | |
| 2004/0071716 A1 * | 4/2004 | Jansen et al. | 424/184.1 |
| 2005/0079510 A1 * | 4/2005 | Berka et al. | 435/6 |
| 2005/0130173 A1 * | 6/2005 | Leamon et al. | 435/6 |
| 2005/0221341 A1 * | 10/2005 | Shimkets et al. | 435/6 |

OTHER PUBLICATIONS

Amsellem, Z., et al., "Complete Abolition of High Inoculum Threshold of Two Mychoerbicides (*Alternaria cassiae* and *A. crassa*) When Applied in Invert Emulsion," *Phytopathology*, 1990, pp. 925-929, vol. 80, No. 10.
Batista-Filho, A., et al., "Enhanced Activity of *Beauveria bassiana* (BALS.) Vuill. Associated with Mineral Oil Against *Cosmopolites sordidus* (Germar) Adults," *An Soc. Entomol. Brasil*, 1995, pp. 405-408, vol. 24, No. 2.
Boyette, C.D., "Unrefined Corn Oil Improves the Mycoherbicidal Activity of *Colletotrichum truncatum* for Hemp Sesbania (*Sesbania exaltata*) Control," *Weed Technology*, 1994, pp. 526-529, vol. 8.
Boyette, C.D., et al., "Biological Control of Hemp Sesbania (*Sesbania exaltata*) Under Field Conditions with *Colletotrichum truncatum* Formulated in an Invert Emulsion," *Weed Science*, 1993, pp. 497-500. vol. 41.
Connick, W., et al., "Formulation of Mycoherbicides Using a Pasta-like Process," *Biological Control*, 1991, pp. 281-287, vol. 1.
Connick, W., et al., "An Improved Invert Emulsion with High Water Retention for Mycoherbicide Delivery," *Weed Technology*, 1991, pp. 442-444, vol. 5.
Egley, G., et al., "Water-Corn Oil Emulsion Enhances Conidia Germination and Mycoherbicidal Activity of *Colletotrichum truncatum*," *Weed Science*, 1995, pp. 312-317, vol. 43.

Scholte, E.-J., et al., "Entomopathogenic fungi for mosquito control: A review," *Journal of Insect Science*, 2004, 24 pages, vol. 4, No. 19.
Shabana, Y., et al., "Evolution of *Alternaria eichorniae* as a Bioherbicide for Waterhyacinth (*Eichhornia crassipes*) in Greenhouse Trials," *Biological Control*, 1995, pp. 136-144, vol. 5.
Womack, J., et al., "Mycoherbicide Formulation and the Potential for Bracken Control," *Pestic. Sci.*, 1993, pp. 337-341, vol. 37.
Womack, J., et al., "A Vegetable Oil-Based Invert Emulsion for Mycoherbicide Delivery," *Biological Control*, 1996, pp. 23-28, vol. 6.
Yang, S-M., et al., "Infection of Leafy Spurge by *Alternaria alternata* and *A. angustiovoidea* in the Absence of Dew," *Phytopathology*, 1993, pp. 953-958, vol. 83, No. 9.
Uniqema, "Atlox® 4912 Polymeric Surfactant: High Internal Phase W/O Emulsifier," Technical Bulletin 00-2, 4 pages.
Johnson et al., Biocompatibility test procedures for materials evaluation in vitro. II. Objective methods of toxicity assessment, J. Biomed. Mater. Research (1985), vol. 19 pp. 489-508.
Biocompatibility testing at Pacific Biolabs (2007).
Freund's adjuvant, extract from Wikipedia, en. wikipedia.org (2007).
Famiglietti et al., Photosynthetic Activity of Cyanobacteria in Water-Oil Emulsions; Biotechnology and Bioengineering (1992) vol. 40; pp. 173-178.

Hochkoeppler et al., Photosynthetic activity of plant cells solubilized in water-in-oil emulsions, Biotechnology and Bioengineering (1991), vol. 37, pp. 918-921.

Srivastava et al., Influence of water on the primary photosynthetic activity of *Rhodospirillum rubrum* in reverse micelles; Photosynthetica (2000), vol. 38 pp. 333-341.

* cited by examiner

*Primary Examiner*—Herbert J Lilling
(74) *Attorney, Agent, or Firm*—Townsend and Townsend and Crew LLP

(57) ABSTRACT

Storage stable compositions of biological materials, including bioactive biological materials are provided in the form of a water-in-oil emulsion, comprising:

(a) cellular material selected from living and/or dormant prokaryotic and/or eukaryotic cells and tissues, the cellular material being compatible with water-in-oil emulsions;

(b) one or more oils selected from vegetable oils and fish oils;

(c) an oil-soluble nonionic polymeric surfactant having a molecular weight of from about 2500 to about 15000; and (d) water.

The compositions may also contain a thickener such as a hydrophobic fumed silica or bentonite.

Compositions may be used for various purposes, depending on the contained biological material. Specific examples include compositions containing *Fusarium lateritium* control of *Eutypa lata* in plant wounds made by cutting or pruning, and compositions containing *Lagenidium giganteum* for control of mosquitoes.

8 Claims, 7 Drawing Sheets

Formulations containing *L. giganteum* after four weeks of storage

Storage time of *Lagenidium giganteum* formulations (days)

STORAGE STABLE COMPOSITIONS OF BIOLOGICAL MATERIALS

STATEMENT AS TO RIGHTS TO INVENTIONS MADE UNDER FEDERALLY SPONSORED RESEARCH OR DEVELOPMENT

This invention was made with Government support of Grant No. 03-03462 awarded by the U.S. Department of Agriculture. The Government has certain rights in this invention.

BACKGROUND AND FIELD OF THE INVENTION

This invention relates to novel compositions or formulations of biological or cellular materials, including but not limited to compositions containing materials such as fungi, watermolds (Oomycetes), algae, yeasts, some bacteria, and plant, insect and animal cells, that are in the form of water-in-oil emulsions (also known as "invert emulsions"). The compositions of this invention demonstrate improved storage stability over known invert emulsions, with the material retaining viability after storage, even without refrigeration.

Materials useful in the compositions include biopesticides such as biofungicides, bioherbicides and bioinsecticides, microbial materials useful in the food, pharmaceutical, waste treatment, pulp and paper, and other industries, and, in general, plant, insect and animal cellular material. The emulsion maintains cell viability, i.e., after storage in the emulsion the stored cells can be added to media and immediately start to grow.

In more specific aspects this invention relates to novel formulations and methods of use of fungal agents such as *Fusarium lateritium* to control infections of plants (notably grapevines), such as *Eutypa lata* infections, through wounds made in cutting or pruning, and to novel formulations of entomopathogenic (insecticidal) bioactive agents such as *Lagenidium giganteum* and their use, for instance to control mosquitoes.

One of the most significant pathogens of the grapevine industry (whether the grapes are grown as table grapes, for raisins, or for wines) is the fungal pathogen *Eutypa lata*, the causative agent for *Eutypa* dieback, commonly known as "dying arm". This pathogen also affects other perennial crops. The disease is spread by the release of ascospores during rainfall; they enter the vascular tissue of a vine through pruning wounds, which are susceptible to infection for up to four weeks after pruning. Infections lead to yield reduction and eventual death of the vines. However, symptoms only appear after the canker is well established, which can be 2-4 years after the initial infection. When the disease is established, incidence can range upwards of 90% in 20-year-old vineyards.

*E. lata* infection is typically controlled by manual application of chemical or biological fungicides to pruning wounds during susceptible periods. However, this is a very labor-intensive process as the fungicide must be manually applied ("painted on") to the individual pruning wounds. Chemical fungicides typically remain viable for only about one week, so that 4-6 applications are needed each season. One fungicide that has been used for this purpose is benomyl. However, the primary manufacturer (DuPont) has withdrawn its registration of benomyl for all purposes.

Biological control has been investigated as an alternative to benomyl. *Cladosporium herbarum* and *Fusarium lateritium* have been found effective in trials. However, performance of *F. lateritium* had been found inconsistent in previous studies. For that reason, a combination of benomyl-resistant *F. lateritium* and benomyl was proposed in published U.S. patent application 2002/159980 (Block and VanderGheynst). The two members of this combination could be applied separately, or as a combined formulation, namely a solution containing benomyl in which the *Fusarium* cells are also suspended. However, this is no longer a viable option due to the withdrawal of benomyl from the market. An improved *F. lateritium* product would be very desirable as a benomyl replacement. However, to be commercially viable, such a product must have a reasonable storage life, i.e., it can be packaged, shipped and stored, while maintaining activity, for a period of time that can extend for months. In addition, *F. lateritium* must be applied directly to the pruning wound shortly after pruning. As mentioned earlier, this is typically done by manual "painting" of each wound.

*Lagenidium giganteum* is a watermold that parasitizes the larval stage of mosquitoes. It often is included in lists of fungi but nevertheless is more closely related to diatoms and brown algae. For purposes of convenience, however, the terms "fingi", "fingal", and the like, as used herein, are deemed to include *L. giganteum*. The life cycle begins with a motile zoospore (asexual stage) that seeks out mosquito larvae, attaching to and penetrating the cuticle via a germ tube. The fungus grows inward, eventually filling the body cavity and killing the mosquito larva. The fungus can then be released from the infected cadaver, generating more zoospores that can infect other larvae. The sexual cycle produces oospores that can maintain the fungus during unfavorable conditions, such as long periods of drought. Upon flooding, oospores release infective zoospores to start the cycle again.

A commercial product containing *L. giganteum* was sold for several years under the trademark Laginex® AS. This product, which no longer is on the market, was an aqueous suspension containing 40% wt./wt. *L. giganteum* mycelium colony forming units (CFU), a concentration measured by cell counts per liter. It was sold as a suspension for aerial spraying. One drawback of this product was the lack of long-term storage stability, a general problem with *L. giganteum* (see, e.g., Scholte et al., *J Insect Sci.* 4: 1 (2004). Additionally, the product needed to be refrigerated to maintain stability. In our work, we found that cell suspensions in aqueous systems tended towards clumping, making the resulting product uneven in composition and problematic in aerial spraying Experience has shown that to be useful in the agrochemical or pest control field, a product must have a reasonably long storage life, including under quite different storage conditions, particularly temperature. To be easily marketed and kept available for use as needed, a product may need to withstand temperatures of 100° F. or greater, and as low as freezing. Such temperatures can be encountered in shipping or storing the products, even though attempts are made to maintain storage temperatures within a more reasonable range. Biological materials such as biopesticides are coming into use more and more with the passage of time. However, such materials are generally more sensitive to temperatures than chemicals, and so the concern over storage stability of such materials is becoming greater. Additionally, biological materials tend to have shorter shelf lives than chemical materials, even under well-controlled storage conditions. However, for marketing and distribution through the normal channels, such materials may need to be kept in storage for months, whether by the distributor, the dealer, or the purchaser.

One apparent solution to problems of storage stability would be to produce the bioactive agent in dried form and, indeed, such compositions are marketed for some bioactive agents, such as *B. thuringiensis*. However, drying is not suitable for all organisms. Some are too sensitive to be completely dried; others show difficulties in becoming activated or reconstituted on contact with water.

In a few cases, formulation of mycopesticides (fungal materials that act as pesticides against other organisms including other fungi and weeds) has been done in the form of so-called "invert emulsions", i.e. water-in-oil emulsions (as opposed to the much more typical oil-in-water emulsions). Such formulations are discussed, for instance, in Amsellem et al., *Phytopathology* 80:925 (1990), Connick et al., *Weed Technology* 5:442 (1991), Womack et al., *Pesticide Science* 37:337 (1993), Boyette et al., *Weed Science* 41:497 (1993), Yang et al., *Phytopathology* 83:953 (1993), Boyette, *Weed Technology* 8:526 (1994), Egley et al., *Weed Science* 43:312 (1995), and Womack et al., *Biological Control* 6:23 (1996). These works typically involved mycoherbicides contained in a water-in-oil emulsion, in which the oil often was a vegetable oil such as corn oil. A surfactant was often used, such as Myverol 18-89, a monomeric surfactant. These publications described effectiveness of the application of the pesticide in question, with the testing being done either in glasshouses or at field research stations. However, storage stability was not an essential aspect of the formulations, as they seem to have been prepared specifically for the tests in question, and so would likely not have been stored for any significant time. In addition, the invert emulsions described in such publications proved to be difficult to handle in general, and particularly difficult to spray.

In addition to use in pest control, biological materials such as fungi and the like are useful in the biotechnology, waste treatment or remediation, pharmaceutical, food, and other industries, where they may serve as catalysts, biodegradation agents, fermentation aids, and diagnostic agents among other uses. Here again, storage-stable cultures would be advantageous. Storage-stable cultures of plant, insect, and animal cells would be valuable, for more convenient preservation and storage of such materials in general.

A control agent for *E. lata* that can be applied directly to a pruning wound shortly after pruning, and that will have an effective life of up to 4-6 weeks, would be a very desirable product. Likewise, a product for use in controlling mosquitoes, and containing *L. giganteum* that that would maintain effectiveness after storage, especially if refrigeration is not required, would be very desirable.

The compositions of this invention provide such products.

BRIEF SUMMARY OF THE INVENTION

In one aspect, this invention comprises a composition in the form of a water-in-oil emulsion, comprising:
  (a) cellular material selected from living and/or dormant prokaryotic and/or eukaryotic cells and tissues, the cellular material being compatible with water-in-oil emulsions;
  (b) one or more oils selected from vegetable oils and fish oils;
  (c) an oil-soluble nonionic polymeric surfactant having a molecular weight of from about 2500 to about 15000; and
  (d) water.

In one preferred embodiment, the compositions further contain a thickener, most preferably a hydrophobic fumed silica or bentonite.

In another aspect, this invention provides a general method for pest control comprising applying to a pest, the locus of a pest, or to a locus where control is desired, a pesticidally effective amount of such a composition that contains a pesticidally active biological material. In a further aspect, the invention comprises a method for preventing *Eutypa lata* infection in wounds made in pruning or cutting vines (particularly grapevines) or other plants comprising applying an effective amount of such a composition containing *Fusarium lateritium* to the blade or blades of a pruning or cutting implement that is to be used on the vines or other plants. In a further aspect the invention comprises controlling mosquitoes by applying an effective amount of such a composition containing *Lagenidium giganteum* to a pest, particularly mosquitoes, the locus of the pest, or a locus where such control is desired.

Compositions of the invention provide storage-stable products containing the organism in question, which may be applied or used as needed, in general without dilution. For instance, compositions of the invention may be prepared that may be aerially sprayed, for example to control mosquitoes in aqueous environments without dilution. Additionally, some compositions of the invention can maintain activity for a good length of time, up to weeks, after application. Additionally, some compositions of the invention are biologically active upon direct application (i.e. no dilution or treatment of the formulation is required) to the environment, and maintain activity for the length of time required for adequate biocontrol.

DETAILED DESCRIPTION

In one aspect, this invention comprises a composition in the form of a water-in-oil emulsion, comprising:
  (a) cellular material selected from living and/or dormant prokaryotic and/or eukaryotic cells and tissues, the cellular material being compatible with water-in-oil emulsions;
  (b) one or more oils selected from vegetable oils and fish oils;
  (c) an oil-soluble nonionic polymeric surfactant having a molecular weight of from about 2500 to about 15000; and
  (d) water.

In one preferred embodiment, the compositions further contain a thickener, most preferably a hydrophobic fumed silica or bentonite.

In another aspect, this invention provides a general method for pest control comprising applying to a pest, the locus of a pest, or to a locus where control is desired, a pesticidally effective amount of such a composition that contains a pesticidally active biological material. In a further aspect, the invention comprises a method for preventing *Eutypa lata* infection in wounds made in pruning or cutting vines particularly grapevines) or other plants comprising applying an effective amount of such a composition containing *Fusarium lateritium* to the blade or blades of a pruning or cutting implement that is to be used on the vines or other plants. In a further aspect the invention comprises controlling mosquitoes by applying an effective amount of such a composition containing *Lagenidium giganteum* to a pest, particularly mosquitoes, the locus of the pest, or a locus where such control is desired.

The cellular material is a biologically active (i.e., "viable") material, which may be, or may be derived from, a eukaryotic or prokaryotic organism, from a microorganism or from a higher, more complex organism such as a plant. The material is preferably cellular in nature, and may comprise a group of single cells or a multicellular organism such as plant callus tissue. The cellular material may be what is often termed "bioactive". This term typically refers to viable biological organisms or tissues that may possess an activity or capability to affect either other organisms (for example, biopesticides) or inanimate objects such as chemical substances (for example, bioactive catalysts for chemical reactions or bioremediation agents), or produce an industrial (for example, enzymes), pharmaceutical (for example, antibiotics) or agricultural biochemical (for example, Bt toxin). Organisms that are incorporated in the compositions of this invention must be compatible with water-in-oil emulsions. In general such organisms include fingi, bacteria, watermolds (Oomycetes), actinomycetes, yeasts, plants, insects and animals, as well as other prokaryotic or eukaryotic organisms. The term "cellular" generally means that the material in question is derived from, or composed, of cells and includes such forms as individual cells, spores and mycelia.

The cellular material comprises living and/or dormant prokaryotic or eukaryotic cellular material, including mixtures of living and dormant forms, or of two or more such biological materials, in an appropriate form. The specific form of the organism in a given composition will depend on the specific organism, the use to which the composition is to be put, and the storage conditions that are anticipated to occur.

Fungi that may be included in the compositions include biopesticides and fingi that may be useful in the food, chemical, pharmaceutical, diagnostics and other industries.

For example, mycopesticides may include *Fusarium lateritium, Metarhizium anisopliae* ("green muscarine"), *Metarhizium flaviride, Beauveria bassiana* ("white muscarine"), *Beauveria brongniartii, Chladosporium herbarum, Paecilomyces farinosus, Paecilomyces fumosoroseus, Verticillium lecanii, Hirsutella citriformis, Hirsutella thompsoni, Aschersonia aleyrodis, Entomophaga grylli, Entomophaga maimaiga, Entomophaga muscae, Entomophaga praxibulli, Entomophthora plutellae, Zoophthora radicans, Neozygites-floridana, Nomuraea rileyi, Pandora neoaphidis, Tolypocladium cylindrosporum, Culicinomyces clavosporus, Muscodor albus, Trichoderma* species, the wide variety of *Cordyceps* and its imperfect forms including *Cordyceps variabilis, Cordyceps facis, Cordyceps subsessilis, Cordyceps myrmecophila, Cordyceps sphecocephala, Cordyceps entomorrhiza, Cordyceps gracilis, Cordyceps militaris, Cordyceps washingtonensis, Cordyceps melolanthae, Cordyceps ravenelii, Cordyceps unilateralis, Cordyceps sinensis* and *Cordyceps clavulata*, and mycorrhizal species such as *Laccaria bicolor*. Other mycopesticidal species will be apparent to those skilled in the art.

Fungi useful in the food industry that may be included in the compositions of this invention include the many species of edible mushrooms (which would be included in the form of their spores or mycelia or combination of the two), Mucorales, filamentous fungi such as various species of *Penicillium Aspergillus*, and *Rhizopus.*

Fungi useful in the pharmaceutical or biotechnology industry that may be included in the compositions of this invention include genera of *Penicillium, Aspergillus, Fusarium, Trichoderma* and *Alternaria* (e.g., for the production of secondary metabolites).

Other useful fungi include genera of *Fusarium, Trichoderma, Neurospora*, and *Monilia*, useful for degradation of organic materials, Arbuscular mycorrhizal fingi (AMF), useful as a fertilizer (e.g., U.S. Pat. No. 6,759,232), various white rot fingi such as *Ophiostoma piliferum* and *Schizophyllum commune*, used for degrading pitch and lignin in wood prior to processing (e.g., U.S. Pat. Nos. 5,607,855 and 5,705,383), and organisms that could be inoculated into soil, composts or container media for suppression of plant diseases (e.g., U.S. Pat. Nos. 4,900,348 and 4,642,131).

Watermolds or Oomycetes that may be included in the compositions of this invention include *Lagenidium giganteum*, enzyme-producing organisms such as those of the orders Peronosporales, Saprolegniales, Leptomitales, and Lagenidiales (e.g., U.S. Pat. No. 6,428,993), and fatty acid producing organisms including those of the genera *Mortierella, Pythium, Entomophthora* and *Phytophthora.*

Algae that may be included in the compositions of this invention include *Amphidinum carteri, Chlorella minutissima, Monodus subterraneus, Nannochloris* sp., *Emiliana huxleyi, Isochrysis galbana, Cryptomonas* sp., *Navicula* sp., *Nitzschia* sp., *Phaeodactylum* sp., *Spriulina* sp., and *Thraustochytrium* sp. Algae will typically be included in the compositions in the form of cells. Such compositions may be useful in manufacturing of food products such as polyunsaturated fatty acids (e.g. U.S. Pat. No. 5,340,742, patent WO 92/12711) and proteins (e.g. *Spriulina* food supplements), and for environmental remediation (e.g. metal sorption and decomposition of herbicides by microalgae and cyanobacteria).

Actinomycetes that may be included in the compositions of this invention include those that produce cellulase, and actinomycetes that have been found to produce paclitaxel, namely Streptomycetes, Actinoplanetes, Maduromycetes, Thermomonosporas or Nocardioforms, particularly those belonging belong to the genus *Streptomyces, Actinoplanes, Nocardiopsis, Micromonospora, Actinomadura*, and especially *Kitasatosporia* (U.S. Pat. No. 6,528,301). Actinomycetes could be included in the compositions in the form of cells and mycelia.

Yeasts that may be included in the compositions of this invention include those used in fermentation processes, pharmaceutical and biotechnology industries, food industries and agriculture (e.g. U.S. Pat. Nos. 6,423,310 and 5,633,025).

Bacteria that are compatible with water-in-oil emulsions and thus suitable for use in the compositions of this invention include, for example, *Acinetobacter venetianus, Rhodococcus erythropolis, Rhizomonas suberifaciens* and *Pseudomonas fluorescens*, all of which are useful in waste remediation processes (see, for example, Dorobantu et al., *Applied & Environmental Microbiology* 70:6333 (2004).

Plant cells that may be included in the compositions include *Anchusa officinalis, Thalictrum minus, Coptis japonica, Catharanus Roseus, Dioscora* sp., *Podophyllum versipelle, Coleus blumei, Papaver somniferum, Nicotiana tabacum*, and *Lithospermum erythrorhizon*. Compositions of this invention containing plant cells are useful, for example, for production of industrial chemicals such as dyes (e.g.

Shikonin produced by *Lithospermum erythrorhizon*) and pharmaceuticals. Plants cells could be formulated as a suspension of cells.

The water-in-oil emulsions of this invention will in general contain at least about 10%, and preferably from about 30 to about 60% w/w water. A 50% water emulsion is often optimal for some of the compositions. However, as discussed below, the use of the surfactants of this invention permit the formation of water-in-oil emulsions that contain more than 50% water, up to as much as about 75-80% water, yet remain a water-in-oil emulsion rather than inverting. Typically the droplet size of the water in the emulsion is kept small so that droplets of water do not combine or settle out of the emulsion. The water droplet size also will be much smaller than the size of the cellular material; for example the water droplet size of an emulsion may be about 1/10 the size of the cellular material. For example, if the cells are about 20μ, then the droplets of water may advantageously be about 2μ.

The oil phase of the compositions of this invention is composed of a vegetable oil and/or a fish oil. The oil may be of any suitable grade, either relatively pure or relatively coarse or unrefined, depending on the use to which the composition is to be put. For example, if the composition is to be applied by aerial spraying, then a relatively inexpensive grade of oil may be used, so long as it forms emulsions having the desired characteristics and performance. On the other hand, if the compositions are to be used for production of foods or of fine chemicals, a higher-grade oil probably should be used.

Suitable vegetable oils include (but are not limited to) corn oil, cottonseed oil, canola oil, peanut oil, soybean oil, wheat germ oil, safflower oil, castor oil, olive oil and sesame oil. Suitable fish oils include those obtained from oily fish such as menhaden, and cod liver oil.

The oil phase of the compositions of this invention may also contain a minor amount of other types of oils such as paraffin oil, mineral oil and the like, so long as they do not provide any deleterious effects to the composition or to the viability of the cellular material formulated therein.

The type of surfactant is an essential component of the compositions, as it is the primary factor that produces a water-in-oil emulsion as opposed to an oil-in-water emulsion, even if the water content is over 50%. In addition, the choice of surfactant determines the long-term physical stability of the water-in-oil emulsion.

The surfactants useful in these compositions are nonionic polymeric oil-soluble (that is, soluble in an oil to the extent used in the compositions) surfactants having a molecular weight of from about 2500 to about 15,000.

In one embodiment the surfactant is a polymeric surfactant having a central section comprising poly(ethylene)oxide ($—OCH_2CH_2—$) units and two side arms comprising a polyester of a hydroxy fatty acid, notably 12-hydroxystearic acid. Such a surfactant has the general formula (I):

(I)

wherein m has a value of from about 5 to about 15 and n has a value of from about 15 to about 35. Surfactants of this type have a molecular weight of from about 5000 to about 10,000, preferably from about 6500 to about 8500, and an HLB value of from about 4.5 to about 6.5, preferably from about 5.0 to about 6.0.

Surfactants of this type include Atlox® 4912 surfactant, which is a block copolymer of polyethylene glycol and 12-hydroxystearic acid having a minimum number average molecular weight of 5000, a product of Uniquema, a member of the ICI Group of companies. This surfactant has 34 poly (ethylene)oxide units in the central section and 7 hydroxystearate moieties in each side arm, and has an HLB value of 5.5. The central section is hydrophilic, the side arms hydrophobic. Its chemical structure is depicted generally in FIG. 1 (note, however, that this figure represents this surfactant only generally, as Atlox 4912 contains a greater number of poly (ethylene) oxide units and hydroxystearate units than depicted.

A second type of surfactant is a nonionic comb-like polymeric surfactant. By "comb-like" is meant that the molecule contains a hydrophilic backbone portion and three or more lipophilic side arms extending outwards from the backbone like teeth on a comb. Structures of comb-like surfactants generally resemble that of Atlox 4912 shown in FIG. 1, but have a longer backbone and three or more side arms or "teeth" of a comb, as opposed to two side arms for Atlox 4912. Surfactants of this type suitable for use in the compositions of this invention are nonionic comb-like polymeric surfactants where the backbone of the comb is composed of succinic acid polyethylene glycol units, and the teeth of the comb are composed of polyisobutylene chains.

Such surfactants have the general formula (II):

(II)

wherein R is polyisobutylene.

A third type of surfactant is a nonionic comb-like polymeric surfactant where the backbone of the comb is composed of polyvinylpyrrolidone units and the teeth of the comb are composed of eicosene ($C_{20}$) groups. Such surfactants have a general molecular structure of formula (III):

$$\left( \begin{array}{c} R \\ | \\ C \\ | \\ R \end{array} \begin{array}{c} R \\ | \\ CH \\ | \\ \end{array} \right)_n \quad \text{(III)}$$

(structure with pyrrolidinone ring bearing R groups, N, and =O)

wherein R is eicosene, $CH_3(CH_2)_{19}$—.

One commercially available surfactant of this type is Ganex® V-220, available from International Specialty Products.

The surfactant is present in the compositions in an amount of from about 0.5 to about 10, preferably from about 1 to about 5, % by weight.

In a preferred embodiment, the compositions also contain from about 0.1% (w/w) to about 3, preferably from about 0.5% to about 1, wt. % of a thickener. The preferred thickeners are hydrophobic fumed silicas, for example R974 from Degussa. However, other thickeners such as bentonite, castor wax, magnesium stearate, and aluminum/magnesium hydroxide stearate, are also suitable for these compositions.

In addition to the ingredients mentioned above, the compositions of this invention may comprise additional substances typical for the type of product involved. They may contain, for example, ultraviolet light protectants, humectants, and nutrients for the organisms, and such other ingredients as are often contained in compositions of cellular materials for the various purposes for which the compositions of this invention are useful, providing, of course, that any additional ingredients do not produce adverse effects on any of the components of these compositions or on the properties of the water-in-oil emulsions. The compositions that contain bioactive materials may also contain chemical active agents, either for the same purposes as the bioactive materials (for example, a co-pesticide), or for a different purpose (for example, a pesticide to control a different pest), providing that such chemical substance is not toxic to the biological material or does not adversely affect its bioactive properties. For example, *Lagenidium* (except in the dormant oospore stage) is in general very susceptible to many pesticides used by mosquito abatement districts or that are applied to crops. Most of the recommended application rates of these pesticides are below levels that are toxic to *Lagenidium*. However, care should be taken if it is desired to incorporate pesticides into a composition of the invention that contains *Lagenidium* or applying compositions containing that organism to areas that have been, or are to be, treated with chemical pesticides.

In general the water-in-oil emulsions of the invention are produced by mixing the necessary ingredients, in the requisite amounts. Usually, the oil phase (containing the surfactant) and the aqueous phase (containing the biologically active material) are prepared separately, then combined with thickener (if used), with agitation, to produce the emulsion. The ingredients for each phase may be added in any convenient order. One advantage of the compositions of this invention is that since the biological material will be in contact with water in the emulsions, it need not be completely dried, as is often the case in preparing formulated products containing such materials. Thus, the compositions of this invention may conveniently contain bioactive or other biological materials that are sensitive to complete drying. However, since the compositions may be stored for extended periods of time and since concentrated products are desirable, a large fraction of water is generally removed from the biological material by filtration and/or centrifugation and/or sedimentation before it is introduced into the composition.

The compositions of this invention are used in a convenient manner depending on the purpose for which they were prepared. Compositions for use in fermentation processes, generation of food additives, or waste treatment or remediation, are used as is typical in these fields. However, it should be noted that the typical bioactive material in these fields may be in the form of a dry product which is either mixed with other materials or which is activated by first being mixed with water. In the present case, since the product is in the form of a liquid, activation might not be needed.

In general the compositions are used as prepared, and are not diluted. Indeed, being water-in-oil emulsions, they could only be diluted with oil, which is impractical. Thus, a composition will be prepared having the concentration of cellular material that is needed for the intended purpose. For example, compositions of the invention for use in degrading pitch and lignin in wood may be supplied in a container and painted or sprayed onto the wood. Compositions of the invention that are intended to be used in a much larger volume of liquid, for example, for use in fermentation tanks, will still be provided at the appropriate concentration of cellular material; however, it is understood that the emulsion will break once the composition has been introduced into the process.

In the case of emulsions containing *Lagenidium* for mosquito control, the compositions of the invention are preferably applied by spraying, most preferably by aerial spraying, in undiluted form. As compared to prior art pesticidal invert emulsions, which were difficult to handle, the compositions of this invention are easy to apply, and disperse readily when sprayed through the spray nozzles typically used.

*Lagenidium giganteum* is very selective to mosquito larvae and in general has not been found harmful to other insects, humans or wildlife. Spraying may advantageously be done over any watery area where mosquitoes may be present, including rice paddies, soybean plantings, marshes, wetlands, drainage dishes, flood plains, wildlife ponds, irrigated pastures, small containers, and the margins of rivers and streams. Susceptible genera include *Aedes, Anopheles, Coquelletidia, Culex, Culiseta, Deinocerites, Eretmapodites, Haemagogus, Mansonia, Opifex, Orthopodomyia, Psorophora, Sabethes, Uranotaenia,* and *Wyeomyia*. The application rate will depend on the cell density in the formulation. Generally, about 25 cells/100 ml is needed to obtain reasonable infection with *L. giganteum*.

As mentioned above, certain pesticides that may be used in the areas to be treated with *Lagenidium* can be toxic to that organism. Accordingly, care should be taken in spraying or otherwise applying compositions of this invention that contain *Lagenidium* to areas that recently have been, or soon are to be, treated with pesticides.

Compositions containing *Fusarium* may be applied to control *Eutypa* and other wound infections in the way compositions are usually applied for that purpose; however, in accordance with one aspect of this invention they may be applied in a novel manner. At present, such compositions, which usually contain a chemical fungicide, are manually applied to each wound in a separate step from the pruning or cutting that produces the wound. However, in one aspect of the present invention, the compositions are applied at the time of pruning or cutting using a special pruner, pruning shears or other cutting implement having grooves or slots in the cutting blade. The blade is connected by a feed line to a container of the composition such that the composition may be pumped or otherwise fed to the area of the grooves, and composition is retained in the groves or slots such that it is applied directly to the cut or wound at the time it is made, thus eliminating the need for a second person to apply the composition.

Figure 1:
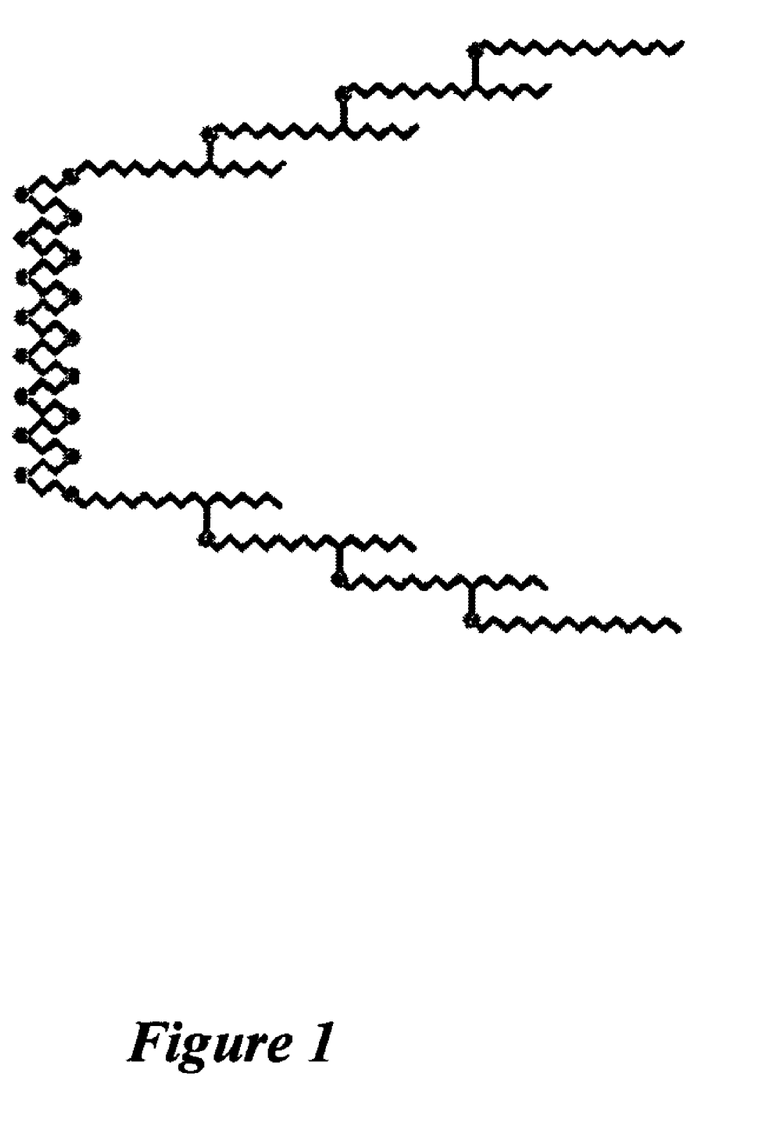
FIG. 1 illustrates the generalized chemical structure of Atlox® 4912 surfactant.
Figure 2:
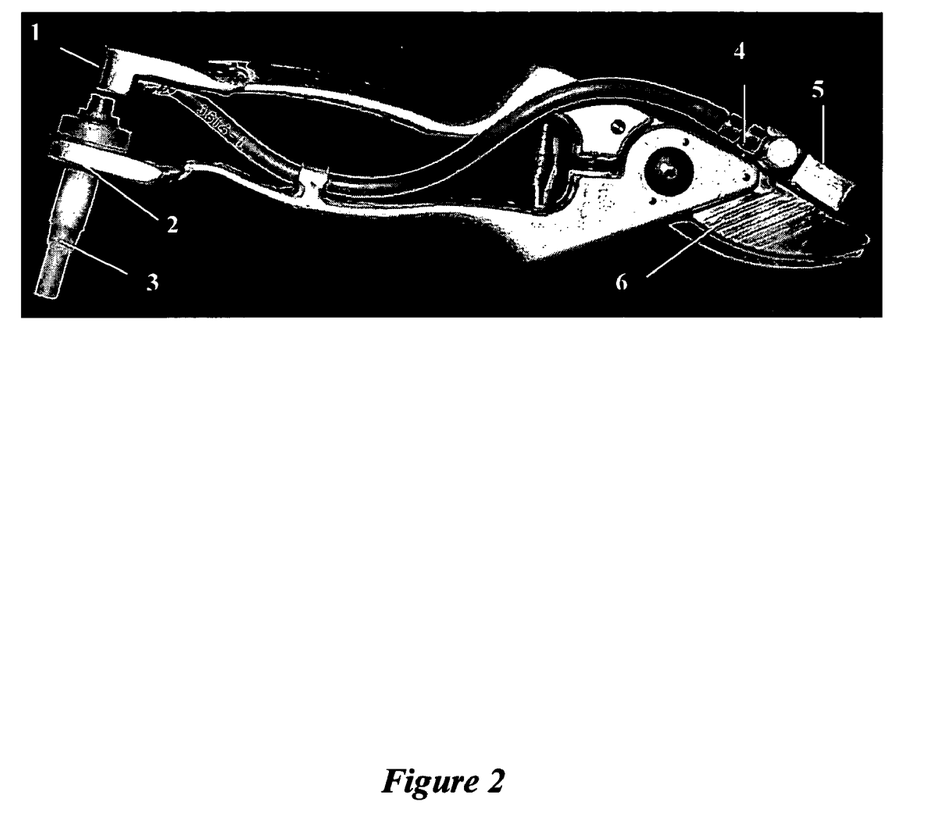
FIG. 2 depicts a specially adapted pruner for use in one aspect of this invention.

FIG. 2 shows such a pruning/formulation application device. The numbers in the figure indicate (1) top handle extension, (2) bottom handle extension, (3) cosmetic pump, (4) hose barb, (5) formulation dispenser, and (6) cutting blade with flat grooves. The prototype pruner consists of a Felco 8 hand pruner (Felco, Les Genevoys sur Coffrane, Switzerland) modified to apply formulation upon cutting grapevine canes. Cutting blade grooves were 1.27 mm deep and 0.787 mm wide, and were milled 1.50 mm apart. A steel dispenser was welded onto the top of each cutting blade. Eight 1.5 mm diameter holes were drilled into one side of the dispenser in two rows of four holes and 1.59 mm cold rolled end caps were cut and welded to the ends. Cold rolled steel was cut into a square piece and welded to the side of the dispenser in order to connect the pump. The dispenser was designed to discharge formulation onto both sides of the blades. The top and bottom handles of the pruner were extended to attach a pump to the end of the pruner handle. The extensions were milled to contour the pump. The pump was a cosmetic pump modified with a hose barb elbow to connect the pump to the dispenser. The pump dispensed approximately 0.5 ml liquid per pump. Plastic tubing was used to connect the pump to the dispenser.

EXAMPLES

The following are examples of compositions of the invention and of their use. However, the inclusion of such examples is not meant in any way to limit the scope of this invention, but merely to provide some illustration of it.

Example 1

This example illustrates a composition according to the invention that contains *Fusarium lateritium* for use in controlling *Eutypa lata* infection of grapevines.

*F. lateritium* and *E. lata* were maintained in shake flask culture-containing potato dextrose broth (difco) (pdb) at 28° C. and 150 rpm, and on potato dextrose agar (pda) plates at 26° C. Liquid cultures were transferred to new media every 10-14 days.

A series of water-in-oil emulsions that contained *F. lateritium* chlamydospores was prepared. The fungus was grown in a medium consisting of onion bulb extract (12 g boiled onion bulb in 1 L ddH$_2$O; 1% w/v) with additional onion plant fibers (10% w/v). Fermentation was carried out for four days at 25° C., pH 4.5 and an agitation rate of 130 rpm, to form the chlamydospores. The oil phase was prepared at least one day prior to formulation by adding from 2 to 14% (w/w) Atlox® 4912 to canola oil. The combined ingredients were maintained at 50° C. for 30 minutes, then stirred at room temperature for another 30 minutes. The emulsions were prepared by combining the chlamydospores with the particular amount of water to form a suspension, adding 0.2, 0.4, 0.6 and 0.8 g/g, of bentonite as a thickener, then mixing that with the oil phase. Compositions containing 20, 30, 40, 50 and 60% (w/w) water were prepared.

Physical stability of *F. lateritium* formulations was measured as the percent (v/v) of visible phase separation after undisturbed storage in 15 ml centrifuge tubes. Colony forming unit density of formulations was measured periodically to evaluate the biological stability of *F. lateritium* formulations. Each formulation was serially diluted in water, and then aliquots of each dilution were spread on the surface of potato dextrose agar (difco). Colonies were counted after 2-3 days of incubation.

*F. lateritium* formulation efficacy was measured using a grapevine bioassay. Bioassays were carried out using Zinfandel grapevine canes-collected from the University of California, Davis experimental vineyard. Canes were stored at −20° C., cut into 5-cm segments and then autoclaved for 30 minutes prior to use. The tip of each autoclaved grapevine segment was cut off using a pruning shear, and then 0.04 to 0.06 g formulation was applied to the cut surface of each remaining segment with a spatula. Controls consisted of segments treated with distilled and autoclaved water and segments treated with an invert emulsion that did not contain *F. lateritium*. The segments were placed into autoclaved bioreactors constructed from 250-ml Nalgene cups with perforated media to support the segments and with inlet and outlet airflow fittings to allow air exchange. To prevent contamination during incubation, 0.22-μm air filters were attached to the airflow fittings. Bioreactors were placed in a 25° C. incubator and aerated at 30-40 ml/min.

To simulate drying of vines that might occur in the field, the bioreactors were supplied air at 0% relative humidity for one day prior to *E. lata* inoculation. Each segment was treated with 25 μl of *E. lata* inoculum or autoclaved distilled water. The *E. lata* inoculum consisted of 4 to 5 day-old maintenance cultures. The cell density in the inoculum Was approximately $10^5$ cells/ml. After treatment of segments with *E. lata* or water, bioreactors were supplied humidified air to promote the growth of *E. lata*. Bioreactors were incubated at 25° C. for ten days.

After incubation the top 1-2 cm of each segment was cut off, sliced in half, and surface disinfected in tubes filled with 25 ml of 2.5% sodium hypochlorite solution with agitation for 30 minutes using a rotary shaker. After surface disinfection, the segments were plated on PDA plates containing 1 mg/l neomycin, bacitracin, and penicillin G, and 25 mg/l chlortetracycline. The PDA plates were then placed in a 25° C. incubator for 7 days.

After this incubation, the plated segments were examined for growth of *F. lateritium* and *E. lata*. Mean percent *E. lata* infection and mean percent *F. lateritium* colonization were calculated by dividing the number of infected or colonized segments by the total number of segments. Mean percent control per treatment was calculated by dividing the number of segments without *E. lata* growth by the total number of segments.

Figure 3:
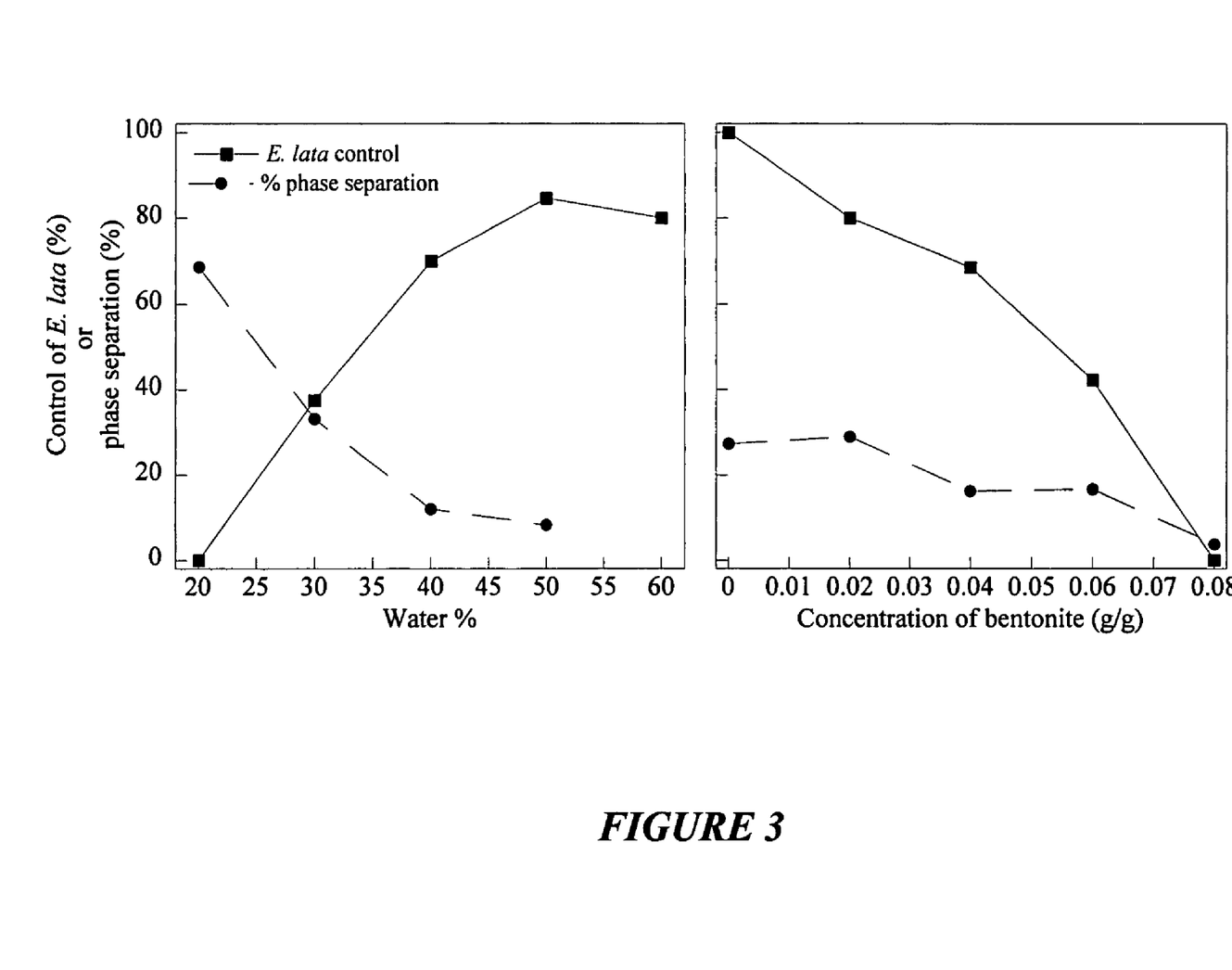
FIG. 3 depicts the effect of amounts of water (a) and bentonite thickener (b) on efficacy and physical stability of compositions of the invention containing *Fusarium lateritium*.
Figure 4:
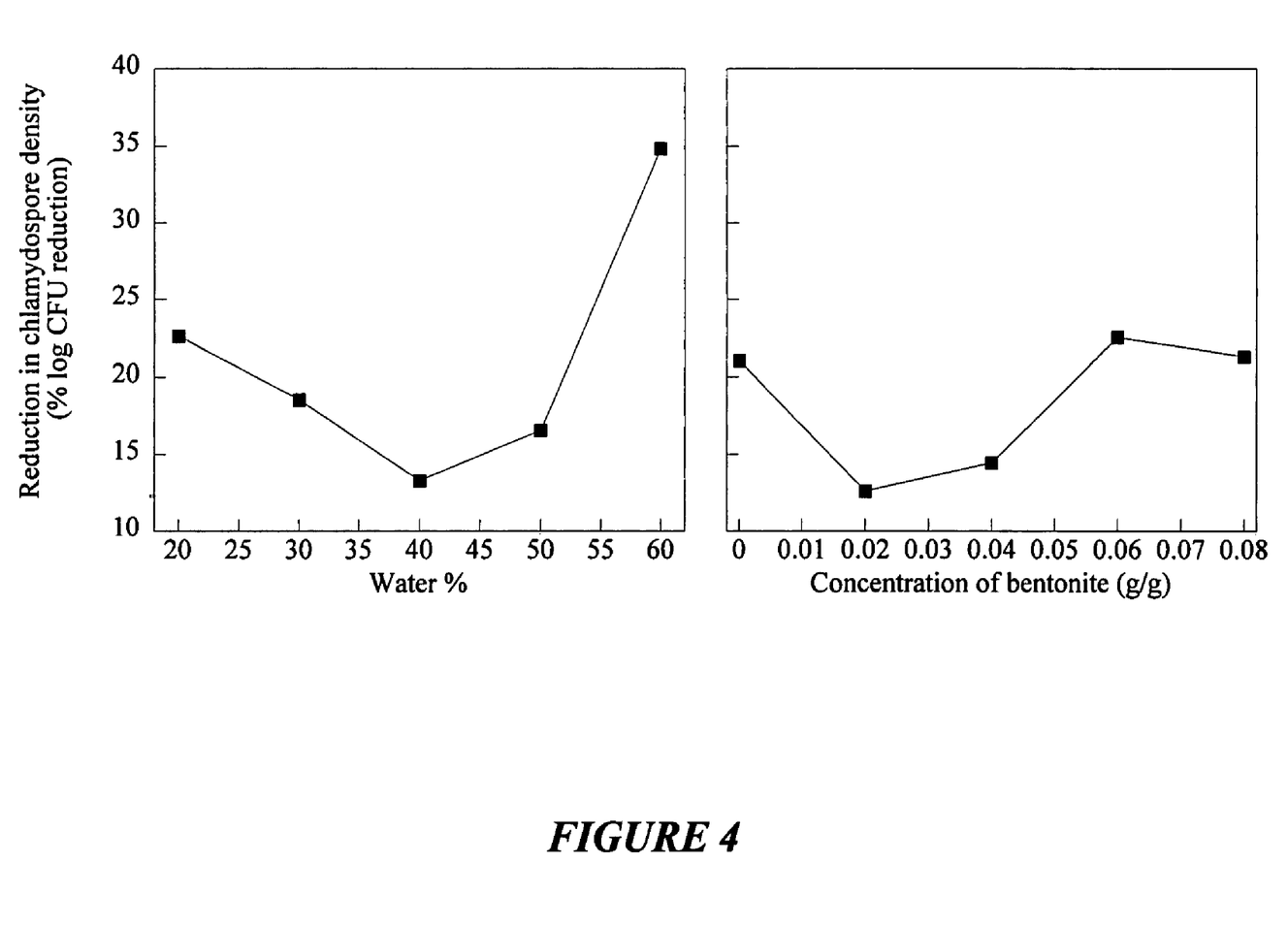
FIG. 4 depicts the effect of (a) water percent and (b) bentonite thickener concentration on the biological stability of *F. lateritium* chlamydospores.

Results of the experiment are shown in FIGS. 3-4.

Efficacy of formulated *F. lateritium* chlamydospores improved as the percentage of water in the emulsion increased (FIG. 3a). However, biological stability was reduced (i.e. percent log reduction increased) when the water content exceeded 50% (w/w). At high water percentages (above 50%) the formulation resulted in a pasty emulsion with physical characteristics that would prohibit it from being applied to a pruning wound using the pruning device described in FIG. 2. As shown in FIG. 3b, bentonite addition improved physical stability (i.e. % phase separation decreased), and small concentrations of bentonite (ca. 0.02 g/g) improved biological stability. However too much bentonite had detrimental effects on the efficacy of *F. lateritium*.

As shown in FIGS. 3a and 3b, efficacy is represented as the control of *E. lata* in grapevine bioassays. Phase separation was determined by measuring the volume of oil separated from the total volume of emulsion. *E. lata* control increased as the percentage of water in the emulsion increased and the concentration of bentonite decreased. Physical stability (decreased phase separation) improved as percentage of water and bentonite concentration increased.

FIG. 4 depicts the effect of (a) water percent and (b) bentonite concentration on the biological stability of *F. lateritium* chlamydospores. Biological stability was calculated as the percent log reduction in chlamydospore density over 112 days of storage. Chlamydospore density was determined by plating serial dilutions of formulations on PDA plates and counting resulting colony forming units (CFU). Biological stability (decreased % log CFU reduction) was optimum at intermediate water percentages and concentrations of humectant.

In one experiment, a commercially available pruning shear was modified to dispense formulated *F. lateritium* chlamydospores onto the cutting blade for direct application onto the pruning wound simultaneously with grapevine cutting. The modified pruner was tested for its ability to cover grapevine pruning wounds using the emulsion formulation. The presence of grooves in pruning blades significantly improved wound coverage (see Table 1 below). The improved coverage may have been a result of grooves wicking the formulation across the blade and increasing the surface area of the blade covered with formulation. Efficacy of formulated *F. lateritium* on pruned grapevine canes was also studied using the pruner for application. There was no significant difference in the mean percent *E. lata* control when formulation was applied by pipette or using the pruners for both 6.35 mm and 12.7 mm diameter canes (Table 2, below). This suggests that formulated chlamydospores were delivered effectively to the vine and the pruner did not affect their biological efficacy.

The modified pruner is shown in FIG. 2. The numbers indicate (1) top handle extension, (2) bottom handle extension, (3) cosmetic pump, (4) hose barb, (5) formulation dispenser, and (6) cutting blade with flat grooves. The prototype pruner consists of a Felco 8 hand pruner (Felco, Les Genevoys sur Coffrane, Switzerland) modified to apply formulation upon cutting grapevine canes. The model is one commonly used in industry. Cutting blade grooves were 1.27 mm deep and 0.787 mm wide, and were milled 1.50 mm apart. A steel dispenser was welded onto the top of each cutting blade. Eight 1.5 mm diameter holes were drilled into one side of the dispenser in two rows of four holes and 1.59 mm cold rolled end caps were cut and welded to the ends. Cold rolled steel was cut into a square piece and welded to the side of the dispenser in order to connect the pump. The dispenser was designed to discharge formulation onto both sides of the blades. The top and bottom handles of the pruner were extended to attach a pump to the end of the pruner handle. The extensions were milled to contour the pump. The pump was a cosmetic pump modified with a hose barb elbow to connect the pump to the dispenser. The pump dispensed approximately 0.5 ml liquid per pump. Plastic tubing was used to connect the pump to the dispenser.

Table 1 shows the mean percent grapevine cane wound covered by the design pruner using cutting blades without grooves and blades with round bottom and flat bottom grooves.[b] The presence of grooves in the blade significantly improved wound coverage (p-value=0.012).

TABLE 1

| | Mean Percent Coverage Area (Standard Error[a]) | | |
|---|---|---|---|
| Blade Type | Cane diameter: 6.35 mm | Cane diameter: 9.525 mm | Cane diameter: 12.7 mm |
| Round grooves | 81.0 (9.4) | 53.4 (6.9) | 64.5 (1.1) |
| Flat grooves | 90.3 (3.7) | 68.0 (3.6) | 70.0 (6.5) |
| No grooves | 53.6 (6.8) | 37.2 (5.3) | 63.5 (9.2) |

[a]n = 5

[b]Area coverage tests were carried out using Zinfandel grapevine canes. Area coverage tests were performed using distilled water in the water phase of the formulation. The tracer pigment T-15 Blaze Orange (Day Glo Color Corp., Cleveland, Ohio) was added to the formulation (1 g/liter) in order to measure percent wound coverage by the formulation.

Table 2 shows the mean percent *E. lata* control and mean percent *F. lateritium* colonization for a grapevine bioassay testing the design pruner. There was no significant difference in the mean percent *E. lata* control or *F. lateritium* colonization when formulation was applied by pipette or using the pruners for both the 6.35 mm and 12.7 mm diameter canes (p-value>0.25).

Bioassay treatments were carried out using Zinfandel grapevine canes collected from the University of California, Davis experimental vineyard, which were cut into 5-cm segments and then autoclaved for 30 minutes prior to use. Autoclaved grapevine segments were cut in half using the design pruner, with and without simultaneous application of formulation, and then placed upright in bioreactors with inlet and outlet airflow fittings to allow air exchange. *F. lateritium*, *E. lata* and water applications with a pipette were done using a volume of 25 µl. Bioreactors were placed in a 25° C. incubator for ten days. After incubation the top 1-2 cm of each segment was cut and surface disinfected in tubes filled with 25 ml of 2.5% sodium hypochlorite solution and agitated for 30 minutes using a rotary shaker. After surface disinfection, the segments were plated on PDA plates containing 1 mg/l neomycin, bacitracin, and penicillin G, and 25 mg/l chlortetracycline. The PDA plates were then placed in a 25° C. incubator for 7 days. After incubation, the plated segments were examined for growth of *F. lateritium* and *E. lata*.

TABLE 2

| Cane diameter (mm) | Treatment application method | Treatment | *E. lata* or water application | Mean % Control (Standard Error[a]) | Mean % *F. lateritium* Colonization (Standard Error[a]) |
|---|---|---|---|---|---|
| 6.35 | pruner | Formulated *F. lateritium* | *E. lata* | 25.93 (26.67) | 100 (0) |
| 12.7 | pruner | Formulated *F. lateritium* | *E. lata* | 37.78 (17.32) | 100 (0) |

TABLE 2-continued

| Cane diameter (mm) | Treatment application method | Treatment | E. lata or water application | Mean % Control (Standard Error[a]) | Mean % F. lateritium Colonization (Standard Error[a]) |
|---|---|---|---|---|---|
| 6.35 to 12.7 | pruner | Formulated F. lateritium | Water | 100 (0) | 100 (0) |
| 6.35 to 12.7 | pruner | Non-formulated F. lateritium | Water | 100 (0) | 100 (0) |
| 6.35 to 12.7 | pruner | Non-formulated F. lateritium | E. lata | 62.44 (13.33) | 100 (0) |
| 6.35 to 12.7 | pipette | Formulated F. lateritium | E. lata | 30 (5.77) | 93.33 (0.33) |
| 6.35 to 12.7 | pruner | Water | E. lata | 0 (0) | 0 (0) |
| 6.35 to 12.7 | pruner | Water | Water | 100 (0) | 0 (0) |

[a]n = 5

Example 2

This Example illustrates a composition comprising *Lagenidium giganteum* and its activity in controlling mosquitoes.

*L. giganteum* (ATCC 52675) was maintained in both liquid and agar media containing 0.025 g cholesterol, 1.25 g peptone, 1.25 g Ardamine pH (autolyzed yeast extract), 3 g glucose, 0.075 g $CaCl_2$, 0.075 g $MgCl_2$, 3 g corn oil, and 0.1 g soybean lecithin (PYGLC) in one liter of distilled deionized water. Liquid cultures consisted of 75 ml of medium in 250 ml Erlenmeyer flasks maintained in an incubated shaker at 26° C. and 150 rpm. Agar cultures (for long term storage) were maintained at 26° C.

*Aedes aegypti* mosquitoes were reared from eggs purchased from Benzon Research (Carlisle, Pa.) and all rearing was completed in a 29° C. incubator. Mosquito eggs were hatched in 500 ml of a 100 mg/l bovine liver powder solution in 15 cm×23 cm×5 cm plastic pans. Each pan contained less than 200 larvae. For each pan, 80-90% of the liquid was decanted and replenished with DI/DO water and 1 ml of a 100 g/l fish-food slurry was added daily. Larvae were ready for bioassays 72 hours after initiating egg hatching.

Formulation: The water and oil phases were combined in a 12-37 ml blender cup (Waring commercial, Torrington, Conn.). To test the effect of thickener addition on stability of the formulation various amounts of silica were added to the cup prior to blending. The cup contents were blended on high using a two-speed industrial blender for 25 seconds.

A series of water-in-oil emulsions that contained *L. giganteum* mycelia were prepared. The oil phase was prepared at least one day prior to formulation by adding 3% (w/w) Atlox® 4912 to refined corn oil. The combined ingredients were maintained at 50° C. for 30 minutes, then stirred at room temperature for another 30 minutes. The emulsions were prepared by combining the mycelia with the particular amount of water to form a suspension, adding 1% of thickener (Degussa R974 fumed silica), then blending that with the oil phase. Compositions containing 50% (w/w) cell suspension were prepared.

Physical stability of *L. giganteum* formulations was measured as the percent (v/v) of visible phase separation after undisturbed storage in 15 ml centrifuge tubes. Colony forming unit density of formulations was measured periodically to evaluate the biological stability of *L. giganteum* formulations. Each formulation was serially diluted in water, and then aliquots of each dilution were spread on the surface of PYGLC. Colonies were counted after 2-3 days of incubation.

Bioassays to examine the control of mosquitoes by the formulations of *L. giganteum* were conducted immediately after making the formulation and after several weeks of storage. *L. giganteum* bioassays consisted of exposing 20 second instar *Aedes aegypti* mosquito larvae to formulations with and without *L. giganteum*. Bioassays were completed in plastic drink cups containing the diluted media and mosquitoes in a total volume of 100 ml. Mosquitoes were fed trace amounts of rat chow on days one and two of the bioassays.

Dead mosquitoes were removed from the bioassay daily and examined microscopically for the presence of hyphal proliferation. Pupae were also removed. Only those mosquitoes displaying *L. giganteum* hyphae were counted as infected. Bioassays were terminated after 7 days.

Figure 5:
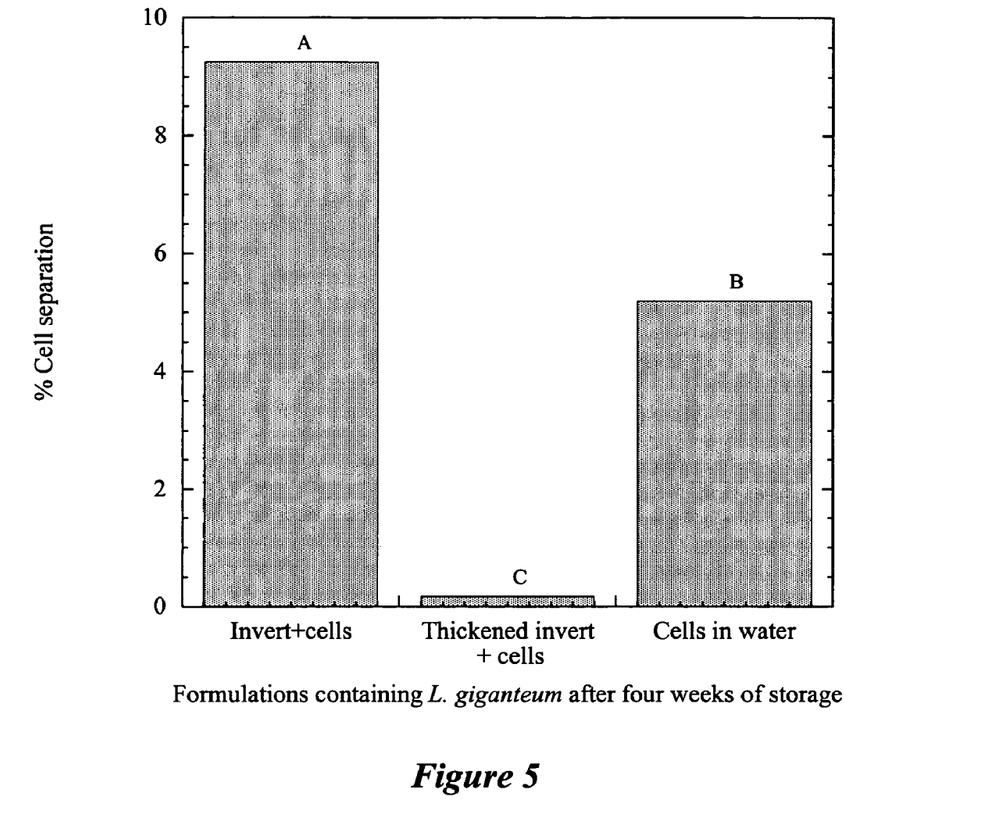
FIG. 5 depicts a comparison of separation of several compositions containing *L. giganteum* cells.

FIG. 5 is a comparison of mean *L. giganteum* cell biomass separation for cells formulated in water, an invert emulsion and an invert emulsion containing thickener. Means with the same letter are not significantly different at $p \leq 0.05$ (n=3). Each formulation was prepared from the same cell suspension and stored for four weeks prior to measuring cell separation. Invert emulsions were prepared using 50% corn oil containing 3% Atlox 4912 and 50% cell suspension. Thickened inverts contained 1% silica. The formulation containing 1% silica showed very little phase separation while the invert with no silica had greater cell separation than cells stored in water. The results demonstrate the need for thickener for preventing phase separation of cells within the invert emulsion.

Figure 6:
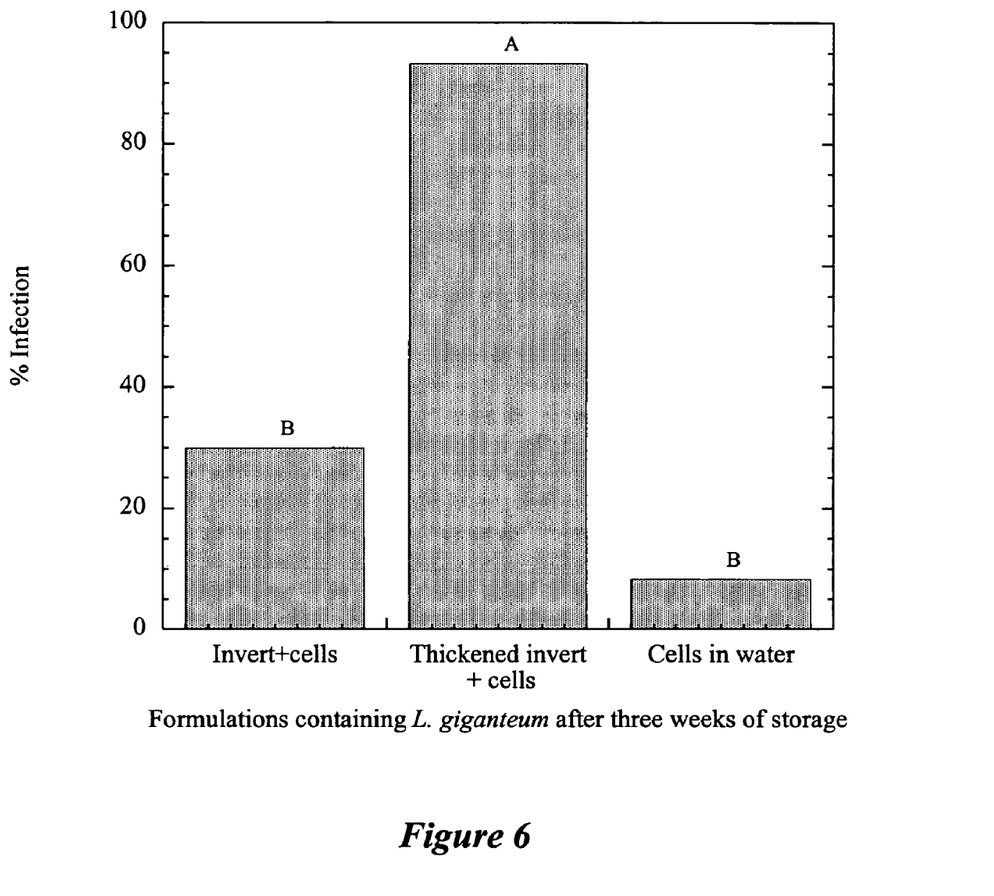
FIG. 6 depicts a comparison of activity of several compositions containing *L. giganteum* cells on mosquitoes.

FIG. 6 is a comparison of mean percent infection in mosquito bioassays testing *L. giganteum* cells formulated in water, in an invert emulsion and in an invert emulsion containing a thickener. Means with the same letter are not significantly different at $p \leq 0.05$ (n=3). Each formulation was prepared from the same cell suspension and stored for three weeks prior to measuring efficacy. Invert emulsions were prepared using 50% corn oil containing 3% Atlox 4912 and 50% cell suspension. Thickened inverts contained 1% silica. Bioassays contained 2 mg formulation per 100 ml. The thickened formulation performed much better than the unthickened formulation and cells formulated in water, indicating that the thickener does not harm the cells, but rather enhances their shelf-life during storage.

Figure 7:
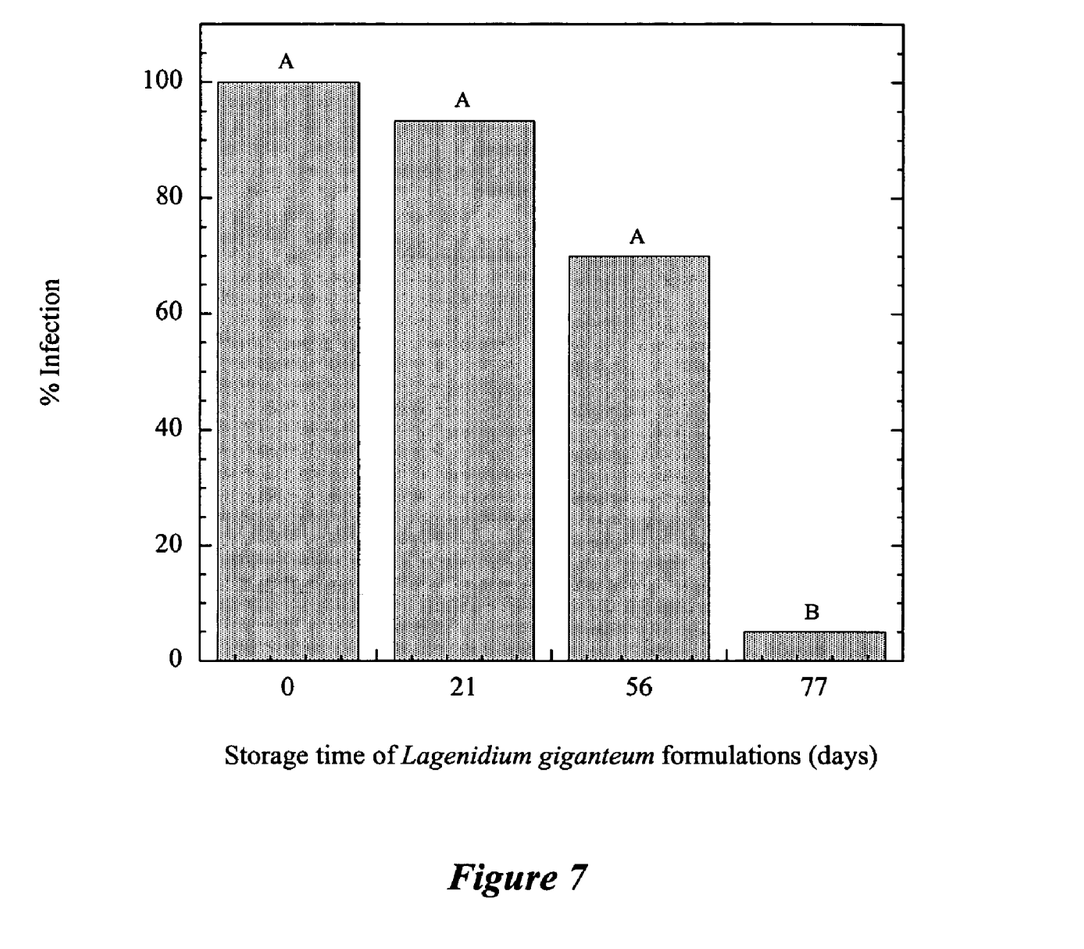
FIG. 7 depicts activity on mosquitoes of a composition containing *L. giganteum* after storage at various times.

FIG. 7 is a comparison of the efficacy of *L. giganteum* cells formulated in thickened invert emulsion after storage times of 0, 21, 56 and 77 days at room temperature (between 22° C. and 25° C.). Means with the same letter are not significantly different at $p \leq 0.05$ (n=3). Invert emulsions were prepared using 50% corn oil containing 3% Atlox 4912 and 50% cell suspension, and also contained 1% silica. Bioassays contained 2 mg formulation per 100 ml. As can be seen from this figure, even after storage for 56 days the formulations maintained a very good activity against mosquitoes.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition in the form of a water-in-oil emulsion, comprising:

(a) living and/or dormant algae cells;

(b) one or more oils selected from the group consisting of corn oil, cottonseed oil, canola oil, peanut oil, soybean oil, wheat germ oil, safflower oil, castor oil, olive oil, and sesame oil, menhaden oil, cod liver oil and mixtures thereof;

(c) an oil-soluble nonionic polymeric surfactant having a molecular weight of from about 2500 to about 15000 and the general formula (I):

(I)

wherein m has a value of from about 5 to about 15 and n has a value of from about 15 to about 35; and (d) water.

2. A composition according to claim 1 containing water in an amount of from about 10 to about 60% (w/w).

3. A composition according to claim 1 containing water in an amount of from about 30 to about 60% (w/w).

4. A composition according to claim 1 containing 50% (w/w) or more water.

5. A composition according to claim 1 further comprising a thickener.

6. A composition according to claim 5 comprising from about 0.1 to about 3% (w/w) of a thickener.

7. A composition according to claim 5 comprising from about 0.5 to about 1.0% (w/w) of a thickener.

8. A composition according to claim 5 in which the thickener is selected from hydrophobic fumed silicas, bentonite, castor wax, magnesium stearate, and aluminum/magnesium hydroxide stearate.